United States Patent
LaRose et al.

(10) Patent No.: US 9,579,433 B2
(45) Date of Patent: Feb. 28, 2017

(54) INTRAVASCULAR VENTRICULAR ASSIST DEVICE

(71) Applicant: HeartWare, Inc., Miami Lakes, FL (US)

(72) Inventors: Jeffrey A. LaRose, Parkland, FL (US); Charles R. Shambaugh, Jr., Coral Gables, FL (US); Daniel G. White, Coral Springs, FL (US); Richard A. Marquis, Miami, FL (US); Steven A. White, Wellington, FL (US); Kartikeyan Trichi

(73) Assignee: HeartWare, Inc., Mounds View, MN (US)

( * ) Notice: Subject to any disclaimer, the term of this patent is extended or adjusted under 35 U.S.C. 154(b) by 0 days.

(21) Appl. No.: 14/171,615

(22) Filed: Feb. 3, 2014

(65) Prior Publication Data

US 2014/0148638 A1    May 29, 2014

Related U.S. Application Data

(60) Continuation of application No. 13/196,693, filed on Aug. 2, 2011, now Pat. No. 8,641,594, which is a
(Continued)

(51) Int. Cl.
| | | |
|---|---|---|
| *A61N 1/362* | (2006.01) | |
| *A61M 1/10* | (2006.01) | |
| *A61M 1/12* | (2006.01) | |

(52) U.S. Cl.
CPC ............ *A61M 1/101* (2013.01); *A61M 1/122* (2014.02); *A61M 1/125* (2014.02)

(58) Field of Classification Search
CPC ........ A61M 1/12; A61M 1/101; A61M 1/125; A61M 1/122; A61M 1/1015; A61M 1/1017
See application file for complete search history.

(56) References Cited

U.S. PATENT DOCUMENTS

| | | |
|---|---|---|
| 4,688,998 A | 8/1987 | Olsen et al. |
| 4,753,221 A | 6/1988 | Kensey et al. |
| (Continued) | | |

FOREIGN PATENT DOCUMENTS

WO    2005032620 A1    4/2005

OTHER PUBLICATIONS

International Search Report issued by the International Searching Authority (ISA/US) in connection with International Application No. PCT/US2008/002484.
(Continued)

*Primary Examiner* — Mallika D Fairchild
(74) *Attorney, Agent, or Firm* — Christopher & Weisberg, P.A.

(57) ABSTRACT

One aspect of an intravascular ventricular assist device is an implantable blood pump where the pump includes a housing defining a bore having an axis, one or more rotors disposed within the bore, each rotor including a plurality of magnetic poles, and one or more stators surrounding the bore for providing a magnetic field within the bore to induce rotation of each of the one or more rotors. Another aspect of the invention includes methods of providing cardiac assistance to a mammalian subject as, for example, a human. Further aspects of the invention include rotor bodies having helical channels formed longitudinally along the length of the body of the rotor where each helical channel is formed between peripheral support surface areas facing radially outwardly and extending generally in circumferential directions around the rotational axis of the rotor.

7 Claims, 13 Drawing Sheets

Related U.S. Application Data division of application No. 12/072,471, filed on Feb. 26, 2008, now abandoned.

(60) Provisional application No. 60/903,781, filed on Feb. 26, 2007.

(56) References Cited

U.S. PATENT DOCUMENTS

| | | |
|---|---|---|
| 4,779,614 A | 10/1988 | Moise |
| 4,846,152 A | 7/1989 | Wampler et al. |
| 4,863,461 A | 9/1989 | Jarvik |
| 4,906,229 A | 3/1990 | Wampler |
| 4,908,012 A | 3/1990 | Moise et al. |
| 4,919,647 A | 4/1990 | Nash |
| 4,927,407 A | 5/1990 | Dorman |
| 4,944,722 A | 7/1990 | Carriker et al. |
| 4,995,857 A | 2/1991 | Arnold |
| 5,092,879 A | 3/1992 | Jarvik |
| 5,112,200 A | 5/1992 | Isaacson et al. |
| 5,211,546 A | 5/1993 | Isaacson et al. |
| 5,256,146 A | 10/1993 | Ensminger et al. |
| 5,290,227 A | 3/1994 | Pasque |
| 5,344,443 A | 9/1994 | Palma, Jr. et al. |
| 5,376,114 A | 12/1994 | Jarvik |
| 5,501,574 A | 3/1996 | Raible |
| 5,509,900 A | 4/1996 | Kirkman |
| 5,527,159 A | 6/1996 | Bozeman, Jr. et al. |
| 5,588,812 A | 12/1996 | Taylor et al. |
| 5,613,935 A | 3/1997 | Jarvik |
| 5,678,306 A | 10/1997 | Bozeman, Jr. et al. |
| 5,692,882 A | 12/1997 | Bozeman, Jr. et al. |
| 5,707,218 A | 1/1998 | Maher et al. |
| 5,746,709 A | 5/1998 | Rom et al. |
| 5,776,190 A | 7/1998 | Jarvik |
| 5,824,070 A | 10/1998 | Jarvik |
| 5,888,241 A | 3/1999 | Jarvik |
| 5,941,813 A | 8/1999 | Sievers et al. |
| 5,947,892 A | 9/1999 | Benkowski et al. |
| 5,965,089 A | 10/1999 | Jarvik et al. |
| 6,015,272 A | 1/2000 | Antaki et al. |
| 6,058,593 A | 5/2000 | Siess |
| 6,068,588 A | 5/2000 | Goldowsky |
| 6,116,862 A | 9/2000 | Rau et al. |
| 6,200,260 B1 | 3/2001 | Bolling |
| 6,227,820 B1 | 5/2001 | Jarvik |
| 6,244,835 B1 | 6/2001 | Antaki et al. |
| 6,254,359 B1 | 7/2001 | Aber |
| 6,299,575 B1 | 10/2001 | Bolling |
| 6,306,116 B1 | 10/2001 | Hancock |
| 6,387,037 B1 | 5/2002 | Bolling et al. |
| 6,390,969 B1 | 5/2002 | Bolling et al. |
| 6,428,464 B1 | 8/2002 | Bolling |
| 6,527,699 B1 | 3/2003 | Goldowsky |
| 6,530,876 B1 | 3/2003 | Spence |
| 6,610,004 B2 | 8/2003 | Viole et al. |
| 6,685,621 B2 | 2/2004 | Bolling et al. |
| 6,716,157 B2 | 4/2004 | Goldowsky |
| 6,716,189 B1 | 4/2004 | Jarvik et al. |
| 6,742,999 B1 | 6/2004 | Nusser et al. |
| 6,794,789 B2 | 9/2004 | Siess et al. |
| 6,889,082 B2 | 5/2005 | Bolling et al. |
| 7,011,620 B1 | 3/2006 | Siess |
| 7,070,398 B2 | 7/2006 | Olsen et al. |
| 7,229,258 B2 | 6/2007 | Wood et al. |
| 2001/0002234 A1 | 5/2001 | Woodard et al. |
| 2003/0233143 A1 | 12/2003 | Gharib et al. |
| 2004/0241019 A1 | 12/2004 | Goldowsky |
| 2006/0036127 A1 | 2/2006 | Delgado, III |
| 2006/0122456 A1 | 6/2006 | LaRose et al. |
| 2006/0245959 A1 | 11/2006 | LaRose et al. |
| 2012/0029265 A1 | 2/2012 | LaRose et al. |

OTHER PUBLICATIONS

Written Opinion of the International Searching Authority issued by the International Searching Authority (ISA/US) in connection with International Application No. PCT/US2008/002484.

International Preliminary Report on Patentability issued by the International Bureau of WIPO on Aug. 26, 2009 in connection with International Application No. PCT/US2008/002484.

Office Action issued Mar. 21, 2011 in connection. with U.S. Appl. No. 12/072,471, filed Feb. 26, 2008.

Office Action issued May 5, 2011 in connection with U.S. Appl. No. 12/072,471, filed Feb. 26, 2008.

First Examination Report issued Jul. 26, 2012 in connection with Australian Patent Application No. 2008219653.

Office Action issued Dec. 16, 2011 in connection U.S. Appl. No. 13/196,693, filed Aug. 2, 2011.

Response to Office Action issued Dec. 16, 2011, filed Jun. 12, 2012, in connection with U.S. Appl. No. 13/196,693, filed Aug. 2, 2011.

Office Action issued Oct. 12, 2012 in connection with U.S. Appl. No. 13/196,693, filed Aug. 2, 2011.

Response to Office Action issued Oct. 12, 2012, filed Apr. 9, 2013, in connection with U.S. Appl. No. 13/196,693, filed Aug. 2, 2011.

Notice of Alloawnce issued Jul. 17, 2013 in connection with U.S. Appl. No. 13/196,693, filed Aug. 2, 2011.

Australian Examination Report for Application No. 2013273663 dated Feb. 25, 2015.

Partial Supplementary European Search Report for Application No. 08726067.5 dated Apr. 17, 2015.

Extended European Search Report for Application No. 08726067.5 dated Sep. 18, 2015.

INTRAVASCULAR VENTRICULAR ASSIST DEVICE

This application is a continuation of U.S. Ser. No. 13/196,693, filed Aug. 2, 2011, now allowed, which is a divisional application of U.S. Ser. No. 12/072,471, filed Feb. 26, 2008, which claims the benefit of U.S. Provisional Application No. 60/903,781, filed Feb. 26, 2007, the content of each of which is hereby incorporated by reference in its entirety into this application.

BACKGROUND OF THE INVENTION

The present invention relates to pumps usable as implantable ventricular assist devices, to components useful in such pumps, and to methods of using the same.

In certain disease states, the heart lacks sufficient pumping capacity to meet the needs of the body. This inadequacy can be alleviated by providing a mechanical pump referred to as a ventricular assist device to supplement the pumping action of the heart. It would be desirable to provide a ventricular assist device which can be implanted and which can remain in operation for months or years to keep the patient alive while the heart heals, or which can remain in operation permanently during the patient's lifetime if the heart does not heal, or which can keep the patient alive until a suitable donor heart becomes available.

Design of a ventricular assist device presents a daunting engineering challenge. The device must function reliably for the desired period of implantation. Moreover, blood is not a simple fluid, but instead is a complex system containing cells. Severe mechanical action can lead to hemolysis, or rupture of the red blood cells, with serious consequences to the patient. Also, blood in contact with an artificial surface, such as the surfaces of a pump, tends to clot. While this tendency can be suppressed to some extent by proper choice of materials, surface finishes and by administration of anticoagulants, it is still important to design the pump so that there are no regions within the device where blood can be trapped or flow is interrupted for relatively prolonged periods. To provide clinically useful assistance to the heart, the device must be capable of delivering a substantial blood flow at a pressure corresponding to normal blood pressure. For example, a ventricular assist device for an adult human patient of normal size should deliver about 1-10 liters per minute of blood at a pressure of about 70-110 mm Hg depending on the needs of the patient.

One type of ventricular assist device or pump uses a balloon. The balloon is placed within the aorta. The balloon is connected to an external pump adapted to repeatedly inflate and deflate the balloon in synchronism with the contractions of the heart muscle to assist the pumping action. Balloon assist devices of this nature have numerous limitations including limited durability and limited capacity.

As described, for example, in U.S. Pat. No. 6,688,861, a miniature electrically-powered rotary pump can be implanted surgically within the patient. Such a pump has a housing with an inlet and an outlet, and a rotor which is suspended within the housing and driven by a rotating magnetic field provided by a stator or winding disposed outside of the housing. During operation, the rotor is suspended within the housing by hydrodynamic and magnetic forces. In such a pump, the rotor may be the only moving part. Because the rotor does not contact the housing during operation, such a pump can operate without wear. Pumps according to the preferred embodiments taught in the '861 patent and related patents have sufficient pumping capacity to provide clinically useful assistance to the heart and can be small enough that they may be implanted within the heart and extend within the patient's thoracic cavity. Pumps of this nature provide numerous advantages including reliability and substantial freedom from hemolysis and thrombogenesis. However, implantation of such a pump involves a majorly invasive surgical procedure.

As described, for example, in Nash, U.S. Pat. No. 4,919,647; Siess, U.S. Pat. No. 7,011,620; and Siess et al., U.S. Pat. No. 7,027,875; as well as in International Patent Publication No. WO 2006/051023, it has been proposed to provide a ventricular assist device in the form of a rotary pump which can be implanted within the vascular system, such as within the aorta during use. Aboul-hosn et al., U.S. Pat. No. 7,022,100, proposes a rotary pump which can be placed within the aorta so that the inlet end of the pump extends through the aortic valve into the left ventricle of the heart.

A ventricular assist device implanted into the vascular system must be extraordinarily compact. For example, such a device typically should have an elongated housing or other element with a diameter or maximum dimension transverse to the direction of elongation less than about 13 mm, and most preferably about 12 mm or less. To meet this constraint, the vascularly-placed ventricular assist devices proposed heretofore resort to mechanically complex arrangements. For example, the device described in U.S. Pat. No. 7,011,620 incorporates an electric motor in an elongated housing. The motor drive shaft extends out of the housing and a seal surrounds the shaft. An impeller is mounted at the distal end of the drive shaft outside of the motor housing and within a separate tubular housing. The pump taught in U.S. Pat. No. 7,022,100 consists of a separate motor using a flexible drive shaft extending through the patient's vascular system to the impeller, with an extraordinarily complex arrangement of seals, bearings, and a circulating pressurized fluid to prevent entry of blood into the flexible shaft. The arrangement taught in WO 2006/051023 and in U.S. Pat. No. 4,919,647 also utilizes flexible shaft drives and external drive motors. These complex systems are susceptible to failure.

Thus, despite very considerable effort devoted in the art heretofore to development of ventricular assist devices, further improvement would be desirable.

SUMMARY OF THE INVENTION

One aspect of the invention is an implantable blood pump. The pump according to this aspect of the invention includes a housing defining a bore having an axis, one or more rotors disposed within the bore, each rotor including a plurality of magnet poles, and one or more stators surrounding the bore for providing a rotating magnetic field within the bore to induce rotation of each of the one or more rotors. The one or more rotors may be constructed and arranged so that during operation of the pump the one or more rotors are suspended within the bore of the housing and out of contact with the housing solely by forces selected from the group consisting of magnetic and hydrodynamic forces. In this embodiment the pump has a maximum lateral dimension in any direction perpendicular to the axis of the bore, or a diameter of up to about 20 mm. In one embodiment the diameter of the bore is about 14 mm. In another embodiment the diameter of the bore is between 9 and 11 mm. The pump of the present invention can impel from about 1-3 liters of blood per minute. In one embodiment the pump is adapted to impel about 2 liters of blood per minute. Blood pressure can be maintained within the range of from 70-120 mm Hg between the inlet and outlet. The pump is adapted for positioning within an artery, and may include a gripper adapted to engage the wall of an artery.

Another aspect of the invention includes methods of providing cardiac assistance to a mammalian subject as, for example, a human. Methods according to this aspect of the invention include advancing a pump including a housing having a bore, one or more rotors disposed within the bore and one or more motor stators disposed outside of the housing through the vascular system of the subject until the pump is disposed at an operative position at least partially within an artery of the subject, and securing the pump at the operative position. The method includes the step of actuating the pump to spin the one or more rotors and pump blood distally within the artery solely by applying electrical currents to the one or more motor stators and to suspend the one or more rotors within the bore solely by forces selected from the group consisting of magnetic and hydrodynamic forces applied to the one or more rotors.

Still further aspects of the present invention include rotor bodies having helical channels formed longitudinally along the length of the body of the rotor. Each helical channel is formed between peripheral support surface areas facing substantially radially outwardly and extending generally in circumferential directions around the rotational axis of the rotor. Each channel has a generally axial downstream portion. The helical and axial portions of each of the channels cooperatively define one or more continuous flow paths extending between the upstream and downstream ends of the rotor. In one embodiment, the axial regions of the channels have greater aggregate cross-sectional area than the one or more passages. The support surfaces of the rotor body are formed on a plurality of lobes. Each lobe has a circumferential extent which increases in a radially outward direction away from the rotational axis of the rotor. The support surfaces face generally radially outwardly away from the rotor axis and define hydrodynamic bearing surfaces. The circumferential extent of the support surfaces is greater than the circumferential extent of peripheral surface areas.

DETAILED DESCRIPTION

Figure 1:
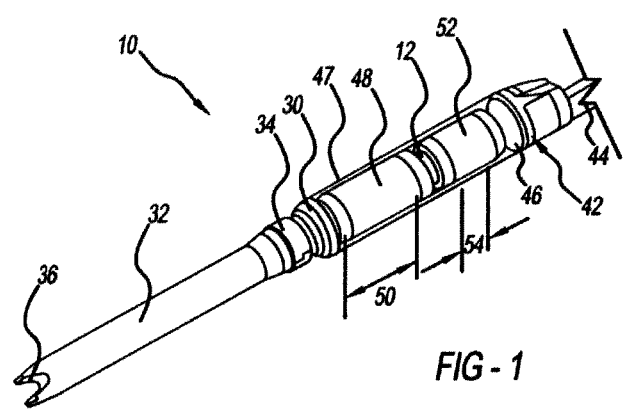
FIG. 1 is a diagrammatic perspective view of a pump in accordance with one embodiment of the present invention, with components omitted for clarity of illustration.
Figure 2:
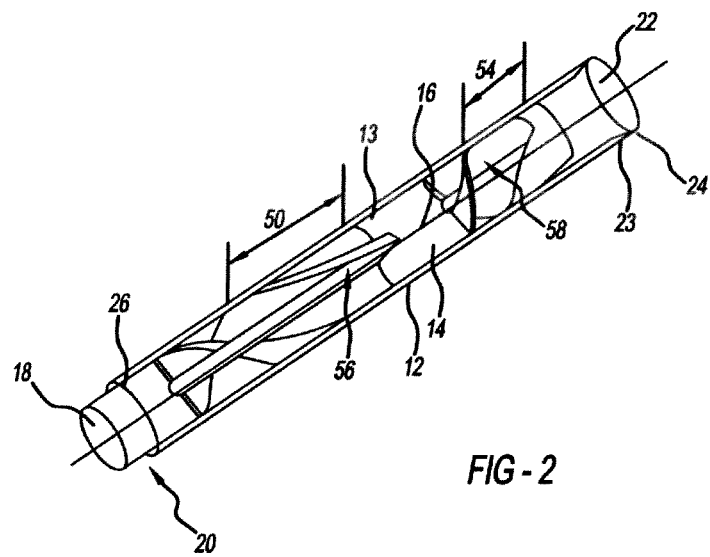
FIG. 2 is a diagrammatic view of components used in the pump of FIG. 1, with certain components depicted as transparent for clarity of illustration.
Figure 3:
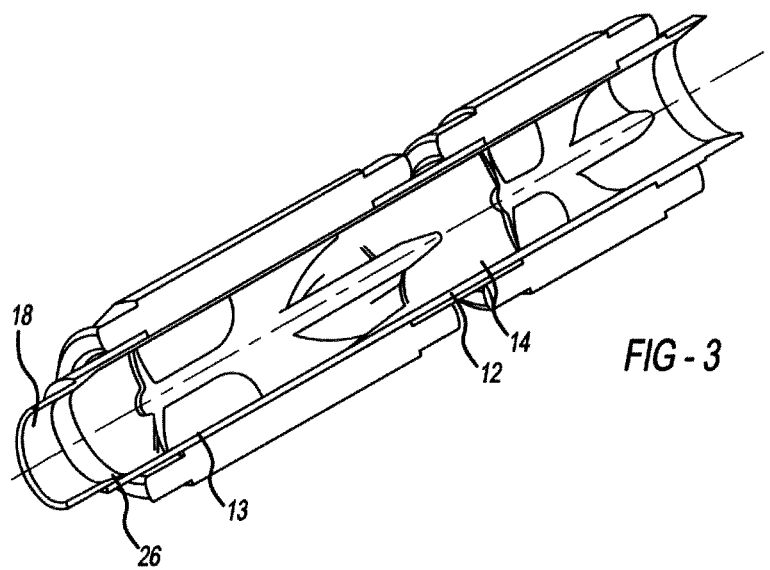
FIG. 3 is a partial cut-away view of the pump depicted in FIGS. 1 and 2.

A pump 10 in accordance with one embodiment of the invention includes a housing 12 (FIGS. 1, 2 and 3). Housing 12 is a ceramic tube defining a central bore 14 having an axis 16. Bore 14 is cylindrical and has a constant diameter over the major portion of its length. The interior surface 13 of the housing defining bore 14 is smooth, and desirably has a surface roughness on the order of 4 micro inches rms or less. Merely by way of example, the inside diameter of bore 14 in this constant diameter region may be about 0.178 inches ("in"), and the wall thickness of the housing may be about 0.010 in. Housing 12 defines an inlet 18 at an end 20 of the housing, referred to herein as the inlet or upstream end, and an outlet 22 communicating with bore 14 at an output or downstream end 24 of the housing. The inside diameter of inlet 18 is slightly less than the inside diameter of bore 14. The housing includes an inlet transition section 26 having an inside diameter which increases progressively in the downstream direction at the juncture between inlet 18 and bore 14. The inside diameter of the housing increases progressively at an outlet transition section 23 immediately upstream from outlet 22.

Figure 4:
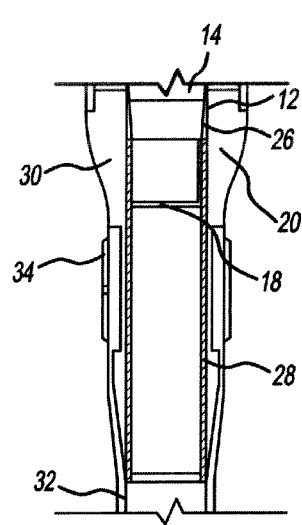
FIG. 4 is a fragmentary sectional view depicting a portion of the pump shown in FIGS. 1-3.

As best seen in FIG. 4, a thin-walled metallic tube 28 is fitted over the inlet or upstream end of the housing so that the interior of tube 28 communicates with inlet opening 18. Tube 28 may be formed from a metal such as titanium, titanium alloy, or platinum, and may be brazed to the ceramic housing. An upstream end fitting 30 surrounds tube 28, and also surrounds the upstream end 20 of the ceramic housing 12. A flexible intake tube 32 surrounds the upstream end of fitting 30 and tube 28, and is held in place by a crimp metal band 34. As best seen in FIG. 1, intake tube 32 extends upstream from fitting 30 and from housing 12, and terminates at a castellated opening 36 at its upstream end. As best seen in FIG. 4, the interior of tube 32 communicates with inlet 18 of housing 12, and thus with the bore 14 of the housing, through tube 28. In one embodiment, intake tube 32 is formed from a non-thrombogenic flexible polymer such as, for example, a fluoropolymer, polydimethylsiloxane, silicone polycarbonate urethanes, thermoplastic polyurethanes, polycarbonate urethanes, segmented polyurethanes, poly(styrene-b-isobutylene-b-styrene, or sulfonated styrene containing copolymers.

A metallic outflow tube 40 (FIG. 5) surrounds the downstream end 24 of housing 12 and communicates with the bore 14 of the housing. Outflow tube 40 may be formed from materials as discussed above with respect to tube 28. The downstream end of outflow tube 40 defines the outlet 41 of the pump 10.

Figure 5:
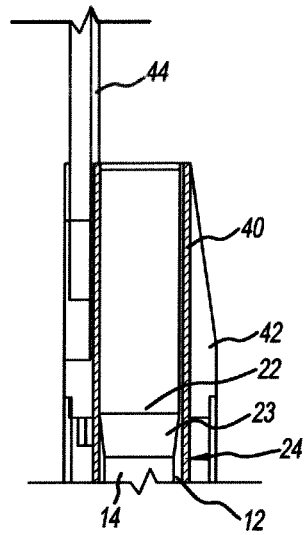
FIG. 5 is a further fragmentary sectional view depicting another portion of the pump shown in FIGS. 1-3.
Figure 6:
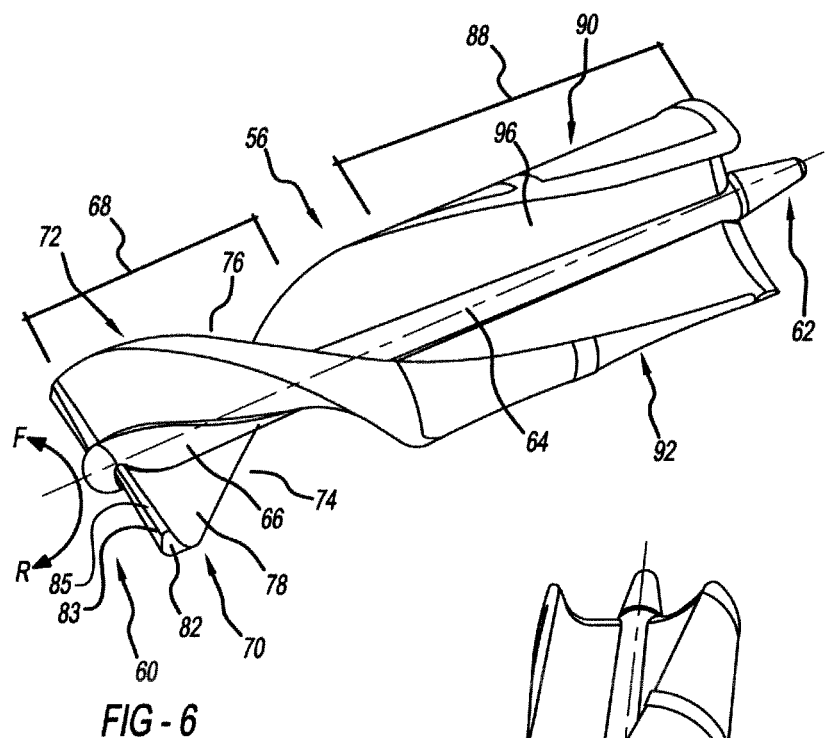
FIGS. 6 and 7 are perspective views depicting a rotor used in the pump of FIGS. 1-5.
Figure 7:
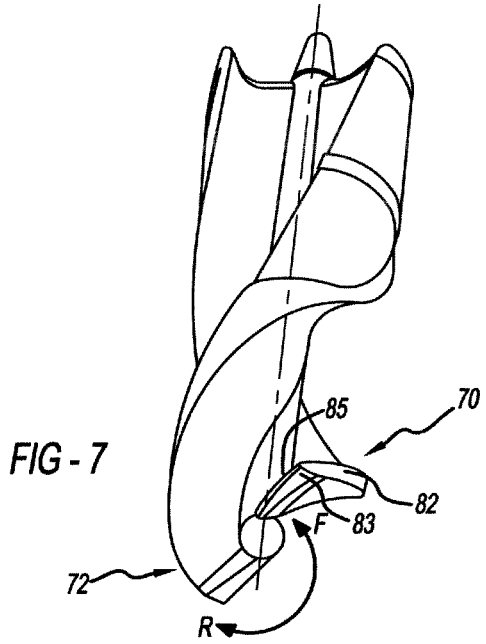

A downstream end fitting 42 surrounds outflow tube 40 and the downstream end 24 of housing 12. An elongated electrical cable 44, of which only a portion is shown in FIGS. 1 and 5, is secured to downstream end fitting 42. As best seen in FIG. 1, the downstream end fitting 42 carries several miniature electrical feedthroughs 46, which are electrically isolated from one another and which are connected to the individual conductors of cable 44.

Figure 25:
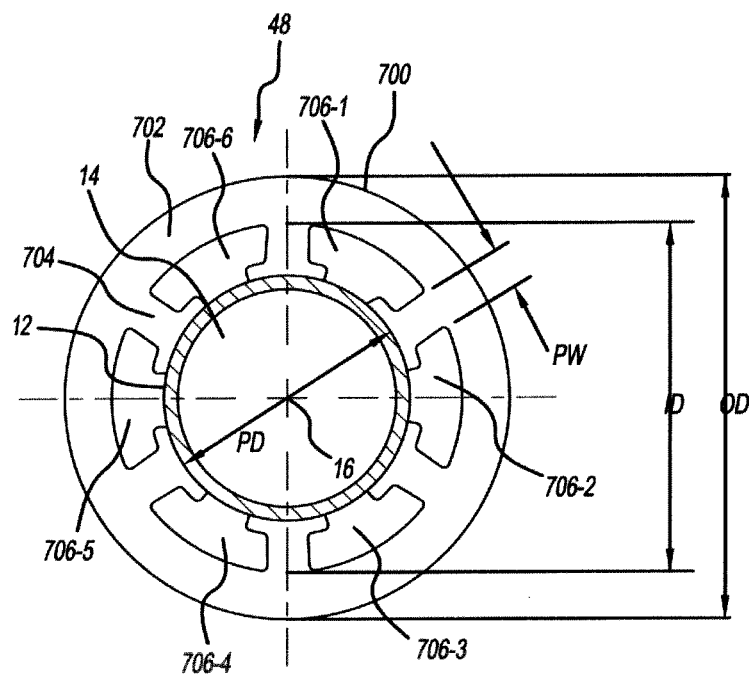
FIG. 25 is a diagrammatic elevational view depicting a component of a stator used in a pump of FIGS. 1-17.

A first stator 48 surrounds housing 12 adjacent the upstream end thereof, shown in FIG. 25. The stator 48 includes a magnetically permeable frame 700. The frame is configured as a cylindrical, tubular ring 702 having a plurality of poles 704 projecting inwardly from the ring 702 to the exterior of housing 12; six poles are used in this particular embodiment depicted. Ring portion 702 is concentric with housing 12 and bore axis 16. Each pole includes a widened portion at the tip of the pole, where the pole confronts the exterior surface of housing 12. The poles define six slots, 706-1 through 706-6, between them. The dimensions of the stator are substantially uniform along the axial length of the stator. In this embodiment the stator is formed from numerous uniform laminations stacked on one another. The laminations are formed from a magnetically permeable material selected to minimize power losses due to magnetic hysteresis. For example, the laminations may be formed from 29-gauge silicon steel of the type sold under the designation M15 electrical steel.

In the particular embodiment depicted, the exterior diameter OD of ring portion 702 is about 0.395 inches, and the interior diameter ID of the ring portion is about 0.304 inches. The width or circumferential extent PW of each pole is about 0.035 inches at its juncture with the ring portion 702. The interior diameter PD between opposed pole tips may be about 0.221 inches. The axial length of the frame is selected according to desired output power, and may be, for example, about 0.35 inches for about 1 watt output to about 0.85 inches for about 3 watts output.

Figure 26:
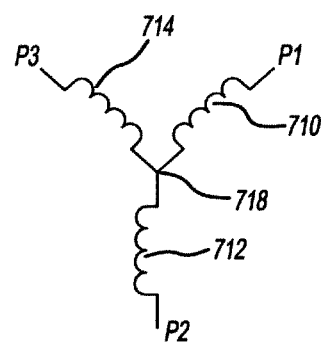
FIG. 26 is an electrical schematic diagram of the stator used in the pump of FIGS. 1-17.

Stator 48 further includes coils 710, 712, and 714 shown in electrical schematic in FIG. 26. In the particular embodiment depicted, each coil includes about 11 to about 14 turns of 33- or 34-gauge insulated wire, and may be impregnated with a material such as a varnish after winding. The coils are connected in a WYE configuration to a common neutral 718. Coils 710, 712, and 714 are disposed respectively in slots 706-1 through 706-6 of frame 700 (FIG. 25). Coil 710 is wound through slots 706-1 and 706-4, whereas coil 712 is wound through slots 706-3 and 706-6, and coil 714 is wound through slots 706-5 and 706-2. This arrangement is commonly referred to as a balanced three-phase integral slot winding. The ends of the coils remote from the neutral point 718 are connected to inputs P1, P2, and P3. When these inputs are energized with three sinusoidal voltages offset from one another in phase by 60°, the coils provide a magnetic field within the bore which is directed transverse to the bore axis 16 and which rotates around the axis, within a first region 50 (FIGS. 1 and 2) of the bore. A second stator 52 is disposed downstream from first stator 48, and is arranged to apply a rotating magnetic field within a second region 54 of bore 14 downstream from the first region. The second stator may be similar to the first stator. Pump 10 further includes a casing 47, depicted in broken lines in FIG. 1, extending between the outflow fitting 42 and the inflow fitting 30, and covering the stators 48 and 52. A potting material (not shown) fills space within casing 47 around the stators.

A first or upstream rotor 56 is disposed within bore 14 adjacent the upstream end of bore, within region the first region 50. A second rotor 58 is disposed within the bore downstream from first rotor 56, within region 54.

The first rotor 56, shown in FIGS. 2 and 6-15, is formed as a solid, unitary body of a ferromagnetic, biocompatible material, such as an alloy including platinum and cobalt, as, for example, an alloy consisting essentially of platinum and cobalt such as 77.3% Pt and 22.7% Co. The rotor has an upstream or inlet end 60, a downstream or outlet end 62, and a rotational axis 64 depicted in dotted line in FIG. 6. The rotor includes a unitary central shaft portion 66 immediately surrounding the axis and coaxial therewith, extending throughout the length of the rotor. The central shaft portion has a generally spherical dome 67 at its upstream end and a conical, tapered region 65 at the downstream end 62.

The body of rotor 56 is described herein with reference to axis 64. As used herein with reference to a structure such as rotor having upstream and downstream ends and an axis, the upstream direction is the direction parallel to the axis toward the upstream end, whereas the downstream direction is the opposite direction. A "radial" direction is a direction outwardly, away from the axis. A "circumferential" direction is a direction around an arc in a plane perpendicular to axis 64. The "forward" circumferential direction indicated by one end F of the arrow FR in FIG. 6 corresponds to the direction of rotation of rotor 56 about axis 64 in service. The opposite circumferential direction indicated by one end R of the arrow FR (FIG. 7) is referred to herein as the reverse circumferential direction.

Figure 8:
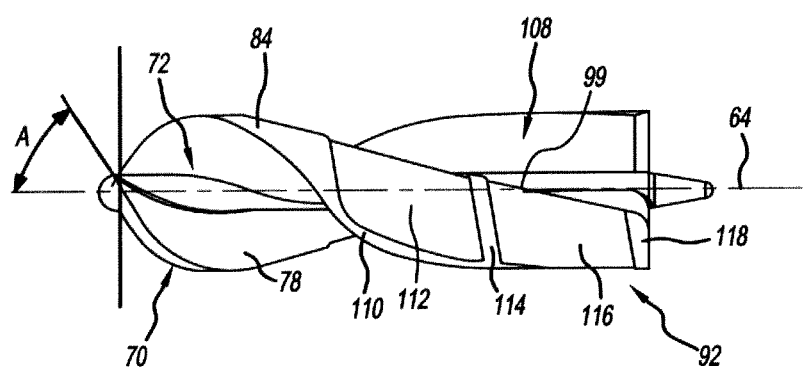
FIGS. 8 and 9 are elevational views of the rotor shown in FIGS. 6 and 7.
Figure 9:
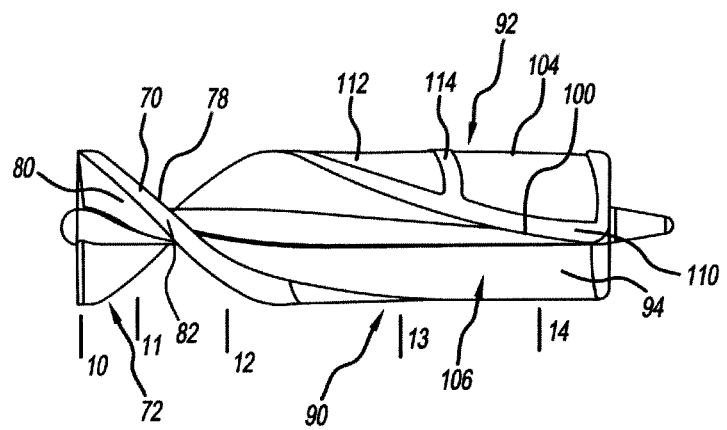
Figure 10:
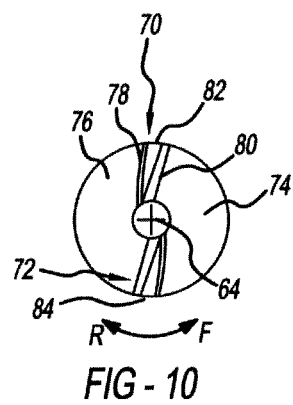
FIGS. 10-14 are sectional views taken along frames 10-14 respectively in FIG. 9.
Figure 11:
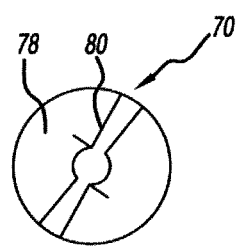
Figure 12:
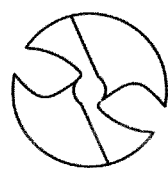

A region 68 of the rotor adjacent the upstream end 60, referred to herein as the "helix" region, rotor 56 has helical channels 74 and 76 defining a pair of raised peripheral surface areas 70 and 72, also referred to herein as vanes 70 and 72, radially outwardly from the central shaft 66. The channel 74 defines a surface area 78 facing in the forward circumferential direction, referred to herein as the pressure surface or, alternatively referred to as the leading surface of vane 70. Pressure surface 78 is a helical surface of variable pitch along the axial length. The pressure surface has a pitch angle A (FIG. 8) of about 60°. As used in this disclosure with reference to a helical surface, the term "pitch angle" refers to the angle between the axis of revolution, axis 64, and a line tangent to the surface. The channel 76 defines a surface area 80, facing in the rearward circumferential direction, referred to herein as the suction surface or alternatively referred to as the trailing surface of vane 70. Suction surface 80 is also helical, but has a slightly larger pitch angle than pressure surface 78, so that the thickness or circumferential extent of raised surface area of vane 70 increases progressively in the downstream direction (to the right as seen in FIG. 9). The suction surface 80 is truncated by a small flat surface 83 in a plane perpendicular to the axis 64 at the upstream end of the helix region, thereby defining a sharp, radially-extensive edge 85, having a radius of about 0.003 inches, at the upstream end of the helix region. The raised peripheral surface area of vane 70 is arcuate and of constant radius about axis 64. The surface area of vane 70 extends through about 130° of arc about axis 64 from its upstream edge to its downstream edge.

Surface area of vane 72 is identical to surface area of vane 70, and is offset from surface area 70 by 180° about axis 64. As best appreciated with reference to the cross-sectional view of FIG. 10, the surface areas 70 and 72 are thin. The circumferential extent of surface area of vane 70 is about 15° of arc around axis 64, and thus the aggregate circumferential extent of surface areas of vanes 70 and 72 amounts to about 30° of arc.

As used in this disclosure, the term "major diameter" of a body having an axis refers to the dimension which is twice the greatest radius from the axis to any point on the body in a particular plane perpendicular to the axis. For rotor 56, the major diameter is simply the length of a line extending between the vanes 70 and 72 through axis 64. As used in this disclosure, the term "solidity" refers to the ratio between the cross-sectional area of the solid features of the body to the area of a circle having a diameter equal to the major diameter of the body. The solidity of the helix portion 68 is in the range of about 10-20% at the upstream or inlet end of the body. In one embodiment the solidity is in the range of about 10-15%, and about 14%, and increases progressively to about 15-25% at the downstream end of the helix region, to about 18-23%. In one embodiment the solidity is about 20%. Stated another way, the helix region is largely open for entry of blood at its upstream end.

The rotor 56 further includes a support region 88 (FIG. 6) disposed downstream from the helix region 68. The rotor has a first lobe 90 and second lobe 92 projecting outwardly from central shaft 66 in the support region. First lobe 90 has a pressure surface 94 (FIG. 9), also referred to as a leading surface, facing in the forward circumferential direction. Pressure surface 94 is continuous with the pressure surface 78 of vane 70. First lobe 90 also has a suction surface 96 (FIG. 6), also referred to as a trailing surface. Suction surface 96 is continuous with the suction surface 80 of vane 70. Thus, the periphery of the first lobe 90 constitutes a continuation of the peripheral surface area of vane 70 in the downstream direction. The first lobe also has a surface 98 (FIG. 13) facing generally radially outwardly away from axis 64, this surface being referred to herein as a "support" surface. The opposite lobe 92 has a similar pressure surface 99 continuous with the pressure surface at area of vane 72, and suction surface 100 (FIG. 9) continuous with the suction surface at area of vane 72. Lobes 90 and 92 are diametrically opposite to one another and define passages 106 and 108 between them. Passage 106 is continuous with channel 74, whereas passage 108 is continuous with channel 76. The passages extend to the downstream end of the body and are open at the downstream end, so that the channels of the helix region and the passages of the support region cooperatively define continuous flow paths extending between the upstream and downstream ends of the body. The pressure and suction surfaces of the lobes have substantially constant pitch angle, and the pitch angles of the pressure and suction surfaces are substantially equal to one another, so that the circumferential extent of each lobe remains substantially constant throughout the support region 88. The pitch angle of the pressure and suction surfaces of the lobes are substantially smaller than the pitch angle of the pressure and suction surfaces in the helix regions. For example, the pitch angles of the lobe pressure and suction surfaces may be on the order of about 10°.

The major diameter of the support section defined by the lobes is equal to the major diameter of helix section. However, as best appreciated by comparison of FIG. 13 with FIG. 10, the circumferential extent of support surfaces 98 and 104 of the lobes is much greater than the circumferential extent of the peripheral edge surfaces 82 and 84 of the helix region. For example, each support surface may have a circumferential extent of about 90-110° of arc about axis 64, so that the aggregate circumferential extent of the support surfaces is about 180-220°. Moreover, the solidity of the support region including the lobes is substantially greater than the solidity of the helix region. The solidity of the support region may be about 30-40%.

Figure 13:
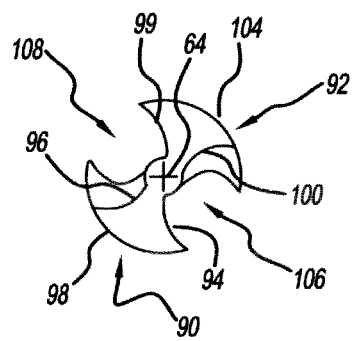
Figure 14:
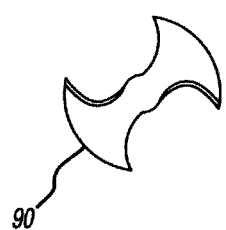

As also apparent from FIGS. 13 and 14, the pressure surface 94 and suction surface 96 of lobe 90 diverge from one another in the radially outward direction, away from axis 64. Similarly, the pressure surface 99 and suction surface 100 of lobe 92 diverge from one another in the radially outward direction. Stated another way, the circumferential extent of each lobe increases progressively in the radially outward direction, so that the mass of each lobe is concentrated in the region of the love remote from axis 64.

Figure 15:
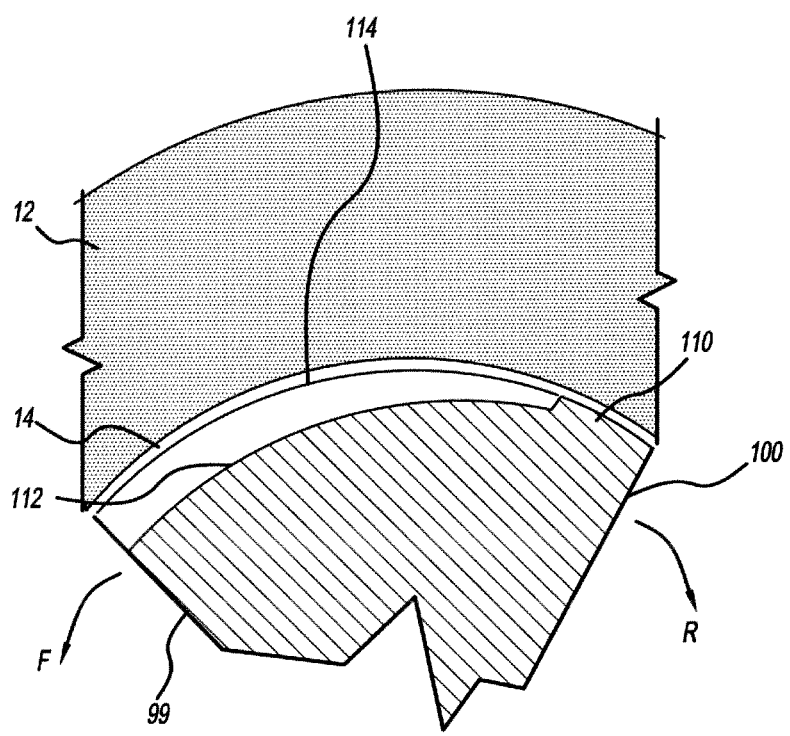
FIG. 15 is a fragmentary, diagrammatic sectional view depicting a portion of the rotor depicted in FIGS. 6-14 in conjunction with another component of the pump.

Support surface 104 of lobe 92 has a trailing land area 110 (FIGS. 8 and 9) disposed at the same radius from axis 64 as the peripheral surfaces of the helix regions. The trailing land area 110 extends along the trailing or suction edge of support surface 104, i.e., the edge of the support surface at its juncture with the suction surface 100 of lobe 92. Land area 110 merges into the peripheral surface 84 of helix area 72, as best seen in FIG. 8. The support surface 104 further includes a first or upstream hydrodynamic-bearing surface 112 and a separating land 114 extending in the forward circumferential direction from trailing edge land 110 to the forward edge of the support surface, at its juncture with pressure surface 99. Land 114 lies at the same radius from axis 64 as the trailing edge land 110. Thus, bearing surface 112 is bounded on its trailing and upstream sides by trailing edge land surface 110 and peripheral surface 84, and on its downstream side by separating land 114. As best seen in FIG. 15, bearing surface 112 is disposed radially inwardly from the land surfaces and slopes radially outwardly towards its trailing edge, i.e., in the reverse circumferential direction toward trailing land surface 110. Stated another way, the land surfaces define a generally cylindrical surface at the major diameter, and bearing surface 112 defines a depression in this generally cylindrical surface which tapers to a decreasing depth in the reverse circumferential direction. As also shown in FIG. 15, the major diameter of the rotor defined by land surfaces 110 is just slightly less than the internal diameter of bore 14 in the housing. For example, the internal diameter of the bore may be about 0.002 inches larger than the major diameter of the rotor.

Support surface 104 further includes a second or downstream bearing surface 116 immediately downstream from separating land 114, and a downstream end land surface 118 immediately downstream of the bearing surface 116. Bearing surface 116 is configured in the same way as bearing surface 112, and forms a similar depression in the cylindrical outer surface tapering to a progressively decreasing depth in the reverse circumferential direction, toward the trailing edge land surface 110.

All of the surfaces of rotor 56 are smooth, desirably to a surface roughness of about 4 micro inches or less. Rotor 56 may be formed, for example, by machining from a solid rod and polishing using techniques such as electropolishing and drag polishing. Rotor 56 has a permanent magnetization with a flux direction transverse to axis 64, so that lobe 92 forms one pole of a permanent magnet, where lobe 90 forms the opposite pole.

Rotor 56 may have an axial length, from the upstream edges of the helix areas to the downstream end of the lobes of about 0.5-0.95 inches, preferably 0.6 inches long. The helix region may be about 0.15-0.25 inches long, preferably about 0.2 inches long whereas the support region may be about 0.35-0.45 inches long in the axial direction, preferably about 0.4 inches long. The ratio between the length of support region and the length of the helix region is about 1:1 to 3:1, preferably about 2:1.

Figure 16:
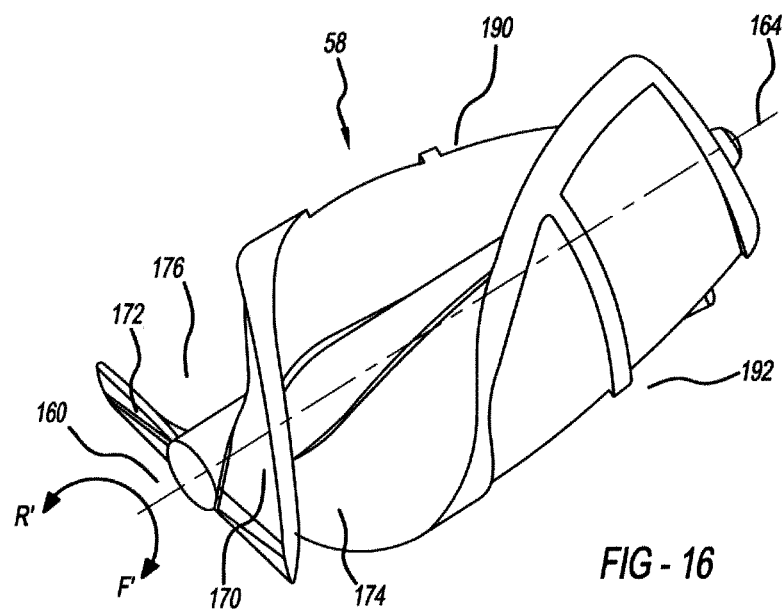
FIG. 16 is a diagrammatic perspective view depicting another rotor utilized in the pump of FIG. 1.
Figure 17:
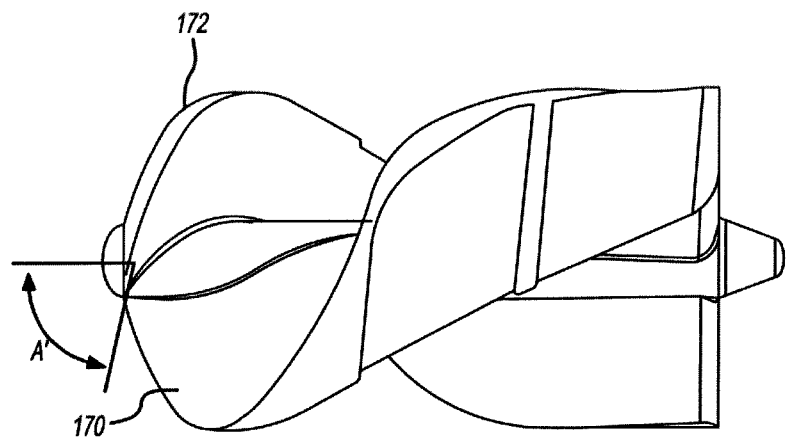
FIG. 17 is a diagrammatic elevational view of the rotor shown in FIG. 16.

The second rotor 58 (FIGS. 16 and 17) is similar to the first rotor 56 discussed above. Thus, the second rotor includes a helix region defined by channels 174 and 176 adjacent the upstream or inlet end 160 of the rotor. The second rotor has lobes 190 and 192 defining passages between them, the passages between the lobes being continuous with the channels in the helix region. Lobes 190 and 192 are configured in substantially the same way as the lobes of the first rotor discussed above with reference to FIG. 13. Thus, in this rotor as well, each lobe has a circumferential extent which increases in the radially outward direction so as to provide a support surface having a substantial circumferential extent. Here again, the solidity of the rotor in the support region occupied by the lobes is substantially greater than the solidity of the rotor in the helix region.

Second rotor 58 has a pitch opposite to the pitch of the first rotor. The forward circumferential direction F' of second rotor 58 is the clockwise direction of rotation about axis 164 as seen from the upstream end 160 of the rotor, whereas the forward circumferential direction of the first rotor 56 (FIG. 6) is the counterclockwise direction as seen from the upstream end 60 of the rotor. Also, the second rotor 58 is substantially shorter in the axial direction than the first rotor. The axial length of the second rotor may be about 0.3-0.5 inches. In one embodiment the axial length is 0.4 inches. Of this length, approximately 0.15 inches is occupied by the helix region, and approximately 0.25 is occupied by the support section consisting of the lobes 190, 192. The pitch angle A' (FIG. 17) of the channel surfaces defining the helix region is substantially greater than the pitch angle A (FIG. 8) of the corresponding surfaces in the first rotor. Here again, each channel surface extends helically around axis 64 by about 130° from the upstream end to its juncture with the associated lobe.

Figure 18:
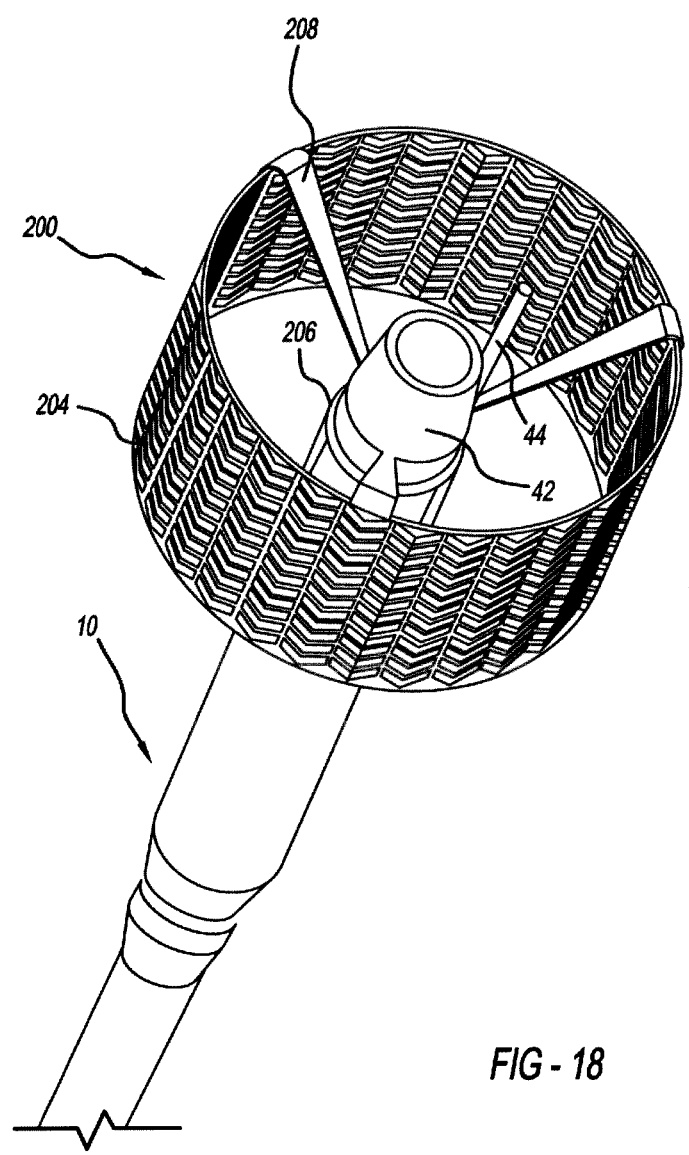
FIG. 18 is a diagrammatic perspective view of the pump depicted in FIGS. 1-17 in conjunction with a further component.

As best seen in FIG. 18, pump 10 desirably is provided with an expansible gripper adapted to engage the interior surface of an artery. Unless otherwise stated, dimensions of the pump referred to herein exclude the gripper. The gripper depicted is a stent 200 which includes a thin-walled cylindrical shall 204 having numerous perforations extending through it. Stent 200 also includes a central collar 206 and three legs 208 which extend from the collar to the downstream edge of shell 204, i.e., the edge of the shell facing upwardly in FIG. 18. Collar 206 is mounted on the outflow end fitting 42 of pump 10 at the downstream or outlet end of the pump. Power cable 44 projects downstream through the interior of shell 204.

In the expanded condition depicted in FIG. 18, stent 204 is spaced radially outwardly from the pump. Stent 204 has a collapsed condition (not shown) in which the stent is disposed downstream from the outlet fitting 42, with legs 208 extending generally parallel to the axis of the pump and downstream from the pump. In this collapsed condition, stent 204 has an exterior diameter approximately equal to or smaller than the exterior diameter of pump 10, i.e., about 13 mm or less. In one embodiment the stent diameter is about 12 mm.

In one embodiment stent 200 is formed from a shape-memory alloy such as the alloy sold under the registered trademark Nitinol™. The stent is initially provided in the collapsed condition, and is arranged to return spontaneously to the expanded condition when the stent is left unconstrained and heated to body temperature.

Figure 19:
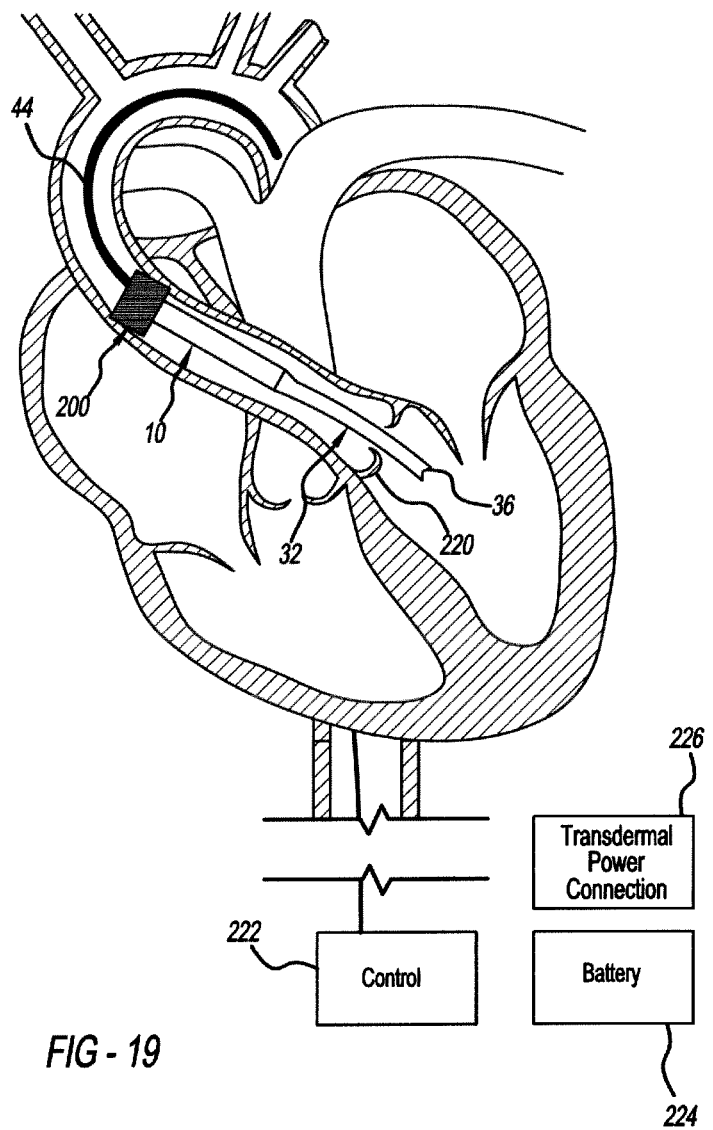
FIG. 19 is a partially blocked diagrammatic view depicting the pump of FIGS. 1-17 in operating position in the cardiovascular system of a subject.

In operation, pump 10 and stent 200 are inserted into the patient's vascular system as, for example, into the femoral artery or another artery having good access to the desired placement site, and advanced through the vascular system, with the intake tube 32 leading, until the pump is in the desired location. As shown in FIG. 19, the pump may be placed within the patient's aorta, with intake tube 32 extending through the aortic valve 220 of the subject's heart, and with the upstream end 36 of the inflow tube protruding into the left ventricle. In this position, power cable 44 extends through the aorta.

The step of advancing the pump through the vascular system may be performed using generally conventional techniques for placement of intra-arterial devices. For example, an introducer catheter may be placed using a guidewire; the guidewire may be removed, and then the pump may be advanced through the introducer catheter, whereupon the introducer catheter is removed. Alternatively, the pump may be provided with fittings suitable for engaging the guidewire. For example, the stent itself may serve as one such fitting at the downstream or output end of the pump, whereas the inflow tube 32 may be provided with a hole (not shown) extending through its wall adjacent its upstream end 36, so that the guidewire is threaded through the interior of the stent and through the hole in the intake tube. In this case, the pump is advanced over the guidewire without using an introducer catheter.

Before or after placement of the pump, the end of power cable 44 remote from the pump is connected to a control unit 222. The control unit 222, in turn, is connected to a storage battery 224. The control unit and battery may be provided as a unitary device in a common implantable housing. Control unit 222 is electrically connected through cable 44 to the stators 48 and 52 of pump 10 (FIGS. 1 and 3), and is arranged to apply appropriate excitation currents to these stators to provide rotating magnetic fields as discussed below. The control unit senses the voltage on the stators and thus detect back EMF generated by rotation of the rotors. The control unit controls the excitations of the stators so as to maintain the rotors at a predetermined speed of rotation. Battery 224 is a rechargeable battery, and is connected to a transdermal power connection 226 Control unit 222. The battery 224 may be implanted in a location within the subject's body outside of the vascular system. The transdermal power connection may include a coil adapted to draw energy from a magnetic field applied through the skin, or may include a fitting extending through the patient's skin and carrying connectors adapted for conductive connection to a power source.

With the pump in place and secured, controller 222 actuates the first or upstream stator to apply magnetic flux within region 50 of housing bore 14 (FIG. 2). The flux direction is transverse to the axis 16 of the housing, and hence transverse to the axis of the first or upstream stator 48. The controller varies the direction of the flux progressively, so that the magnetic field direction rotates about axis 16 in the forward direction of first rotor 56. Because of its permanent magnetization, first rotor 56 aligns itself with the flux direction, and thus spins about its axis at the same rate as the flux. The lobes 90 and 92 provide a strong permanent magnet. Moreover, the magnetic material of the lobes is concentrated near the outside of the stator, in close proximity to the wall of bore 14, and thus in close proximity to stator 48. This provides a strong magnetic interaction between the stator and the rotor. In one embodiment the field and rotor rotate within the range of about 20,000-60,000 revolutions per minute (rpm), most typically about 50,000 rpm.

As the rotor spins about its axis, the bearing surfaces on the lobes advance with the rotor in the forward circumferential direction. As best appreciated with reference to FIG. 15, there is a relatively large clearance (about 0.004 inches) between the interior surface of tube 14 and bearing surface 112 at the forward edge, where the surface intersects forward surface 99 of the lobe. There is a smaller clearance at the rearward edge of the bearing surface, near land 110, where the bearing surface transitions smoothly into the land 110. There is an even smaller clearance between the land 110 and the wall of the housing. Thus, as the bearing surface advances in the forward direction, a high hydrodynamic pressure is created at the rearward portion of the bearing surface. The same is true for the downstream bearing surface 116 (FIGS. 8 and 9), and for the bearing surfaces of the opposite lobe 90. The hydrodynamic pressures keep the rotor centered in the bore and out of contact with the wall of the bore. The land portion 114 between bearing surfaces forms a barrier to axial flow of blood between the upstream bearing surface 112 and the downstream bearing surface 116. The same is true for the bearing surfaces of the opposite lobe. This helps to assure that the bearing surfaces provide independent separating forces at axially spaced locations along the support region of the rotor, so that the rotor resists pitch or yaw of the rotor axis relative to the central axis of the bore.

The magnetic field applied by stator 48 maintains the rotor in axial alignment with the stator, and prevents the rotor from moving axially within the bore. Thus, during operation, the rotor is suspended within the bore by the hydrodynamic and magnetic forces applied to it, and is entirely out of contact with any solid element of the pump. The rotor thus operates with no wear on the rotor or the housing.

As the first rotor spins, the leading and suction surfaces of the channels 74 and 76 (FIG. 6) of the first rotor impinge on blood present within the bore 14 of the housing, and impel the blood downstream. The relatively low solidity provided by the helix region promotes inflow of blood into the flow channels and thus helps to provide effective pumping action. The lobes 90 and 92 provide relatively little pumping action. However, the passages 106 and 108 between the lobes provide a relatively low-resistance flow path from the channels in the helix region 68 (FIG. 6) to the downstream end of the first rotor. As discussed above, the support region 88 and lobes 90 and 92 serve to provide support for the rotor within the bore and to provide an effective drive action. Surprisingly, it has been found that varying the configuration and solidity of the rotors along their axial extent, so that the helical region exhibits relatively low solidity and relatively small peripheral surfaces and the lobes have relatively high solidity and substantial circumferential surfaces, provides a particularly good combination of pumping action with adequate support and adequate magnetic linkage to the rotating flux of the stator.

As the upstream rotor 56 spins about its axis, viscous drag exerted by the rotor and the blood entrained therewith on the blood immediately upstream of the rotor within bore 14 tends to impart a swirling or rotational motion to the blood upstream from the rotor, so that the blood approaching the rotor is already spinning in the forward direction of the rotor. In theory, this effect tends to reduce the pumping action imparted by the rotor. This effect could be mitigated by providing fixed axial vanes inside the bore just upstream from the rotor. However, it is believed that a significant advantage is obtained by omitting such vanes, so that the bore immediately upstream from the rotor is an unobstructed surface of revolution about the central axis 16, with no obstruction to swirling flow. In one embodiment, the unobstructed bore extends upstream from the rotor for at least about 2 times the bore diameter. Leaving the bore unobstructed in this manner provides a gentler action at the upstream end of the rotor and thus tends to reduce hemolysis. Stated another way, limitations on rotor speed which may be imposed by hemolysis considerations are relaxed by providing such an unobstructed bore upstream from the rotor.

All of the surfaces of the rotor and the interior surface of the housing in the vicinity of the rotor are continually washed by flowing blood, so that there is no stasis or pooling of blood. This substantially mitigates the risk of thrombus formation. Moreover, because the rotor operates without wear on the rotor or the housing, the surfaces of the rotor and housing remain smooth, which further reduces thrombogenesis. The rotors constitute the only parts of the pump which move during operation. As the rotors are maintained out of contact with other parts of the pump, the pump has no moving parts which contact one another during operation. In particular, the pump has no seals which contact moving parts during operation. A pump without such seals can be referred to as a "seal-less" pump.

Because rotor 56 is a simple, two-pole magnet, the stator need provide only two flux reversals per revolution. Each flux reversal requires that the control unit and battery overcome the inductive impedance of the stator, and each flux reversal consumes power in hysteresis of the ferromagnetic material in the stator. Accordingly, the frequency of motor commutation required for a given rotational speed is lower for a two-pole rotor than for rotors with a greater number of poles.

The second or downstream rotor 58 operates in substantially the same manner as the first rotor 56, and is suspended within bore 14 of housing 12 by a similar combination of magnetic and hydrodynamic forces. The second rotor spins in the opposite direction from the first rotor. The blood passing downstream from the upstream rotor 56 has a swirling motion in the forward or rotational direction of the first rotor, i.e., in the direction opposite to the direction of rotation of the second rotor. In the particular embodiment illustrated, the downstream or second rotor provides approximately a third of the pumping work performed on the blood passing through the pump, whereas the upstream rotor provides approximately two-thirds of the pumping work. As the magnetic fields associated with each stator apply torque to the rotors to turn the rotors about their axes, an equal but opposite torque is applied to the stators. Because the rotors turn in opposite directions, these reaction torques applied to the two stators tend to counteract one another, and thus reduce the torque load applied to stent 200 (FIG. 19).

Pump 10 in the embodiment described can pump approximately 3 liters per minute against a pressure differential of approximately 100 mm Hg, a typical physiological blood pressure. The pump thus provides substantial assistance to the pumping action applied by the left ventricle of the heart. Moreover, the pump provides this effective pumping assistance in a device that is small enough to be implanted in the aorta using a minimally invasive procedure, and which can operate for extended periods without wear or mechanical failure.

The leaflets of the patient's aortic valve 220 (FIG. 19) seal against the exterior surface of inflow tube 32, and thus prevent backflow of blood into the left ventricle during diastole. When the ventricle contracts, during systole, blood pumped by the heart flows through the aortic valve around the inflow tube and the pump. The pump and the stent do not occlude the aorta, and do not prevent the heart from exerting its normal pumping action. Thus, in the unlikely event of a pump failure, the patient's heart can continue to provide some blood circulation. Depending upon the patient's condition, this circulation may be adequate to sustain life until corrective action can be taken.

Numerous variations and combinations of the features described above can be utilized without departing from the present invention. For example, the second or downstream rotor and the corresponding stator may be omitted to provide a smaller pump with somewhat lesser pumping capacity. Conversely, three or more rotors may be utilized. The dimensions and proportions discussed above can be varied. For example, the housing, rotors and stators can be made with a substantially larger diameter to provide more pumping capacity in a pump which is to be implanted surgically, as for example, by connection through the apex of the heart.

The pump can be positioned in other locations. In one such variant, the intake tube is omitted and the pump is positioned proximally from the position illustrated in FIG. 19, with the inlet end of the pump housing itself protruding through the aortic valve. In yet another variant, the pump may be positioned in the descending aorta, in the femoral artery or in another artery, so as to provide localized circulatory assistance. The pump also may be implanted into a pulmonary artery to provide assistance to the right ventricle.

Figure 20:
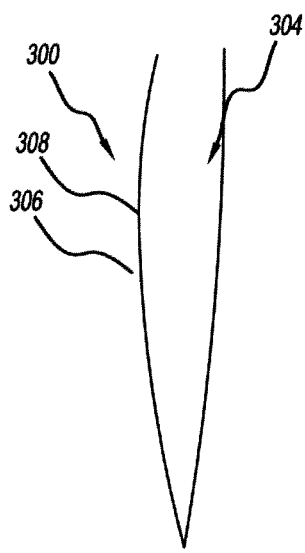
FIGS. 20 and 21 are diagrammatic perspective views depicting components used in further embodiments of the invention.

A pump 310 in accordance with a further embodiment (FIG. 20) includes a gripper 300 having a collar 302 attached to the outflow fitting or shroud of the pump adjacent the downstream or outlet end of the pump, and a set of fingers 304 attached to collar 302 at locations spaced apart from one another circumferentially around the axis of the pump. Each finger has a tip 306 remote from the collar and a crown section having a relatively large circumferential extent disposed near the tip. Each finger also includes a beam section 311 between the crown section 308 and collar 302. In the expanded condition illustrated in FIG. 20, the beam sections 311 project outwardly from the collar 302, and the crown sections have a curvature so that the tips 306 point inwardly toward the axis of the pump. The crown sections 308 bear on the interior wall of an artery (not shown), whereas the tips 306 are maintained out of contact with the artery wall. The beam sections 311 have relatively low resistance to flow of blood in the axial direction. Fingers 304 may be formed from a shape memory alloy as discussed above, and have a collapsed condition in which they project axially and thus lie flat against the exterior surfaces of pump 310. In a variant, the tips 306 may project inwardly toward one another at the upstream or inlet end of the pump to facilitate movement of the pump along the artery during placement.

Figure 21:
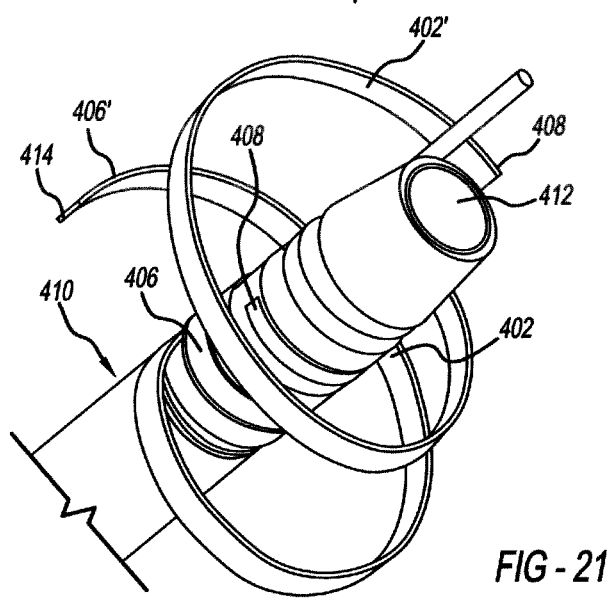

Referring to FIG. 21, a pump 410 according to yet another embodiment of the invention includes a gripper in the form of two strips 402 and 406. In the collapsed condition, strip 406 is wound in a helix, closely overlying the exterior surface of the pump. The downstream end of the strip 406, closest to the downstream end 412 of the pump, is affixed to the pump body. The upstream end 414 is free, and is secured to the pump only by the other turns of the helix. The second strip 402 has its upstream end 409 affixed to the pump body, and its downstream end 408 free to move relative to the pump body, constrained only by the remaining turns of the helix. When the pump is implanted, strip 402 assumes the expanded position shown at 402'. In this condition, strip 402 is generally in the form of a spiral extending clockwise about the axis of pump 410, as seen from the downstream end 412 of the pump. Strip 406 assumes the shape shown at 406' and approximates a spiral with the opposite direction from spiral 402', i.e., extending counter-clockwise from its juncture with the pump body to its free end 414, again as seen from the downstream end 412 of the pump.

Grippers described herein can be configured at intervals along a driveline that extends from the pump to a battery or a controller. Such driveline is downstream of the pump and a configuration of grippers along its length can be used to maintain driveline position in a main path of blood flow and away from arterial walls. The combination of gripper support of the pump and gripper support of the driveline eases the removability of the pump if, for example, repair is needed or the pump is no longer needed by the patient. Driveline gripper supports may be attached to the driveline in intervals of roughly 0.23-0.46 inches along the length of the driveline.

As discussed above, the proportions of the rotors can be varied. More than two lobes and helix sections may be employed. In one embodiment, the number of lobes is equal to the number of helix sections. However, other configurations can be employed. Also, the rotors discussed above have the same major diameter over the length of the pump body so that, considering the major diameter only, the rotor is generally cylindrical. This also is not essential. For example, a rotor may have a helix section with a greater major diameter than the support section. Such a rotor may be used with a tapered housing. The stator may surround only the region of the housing which receives the support region, so that the pump as a whole has a small diameter.

Figure 22:
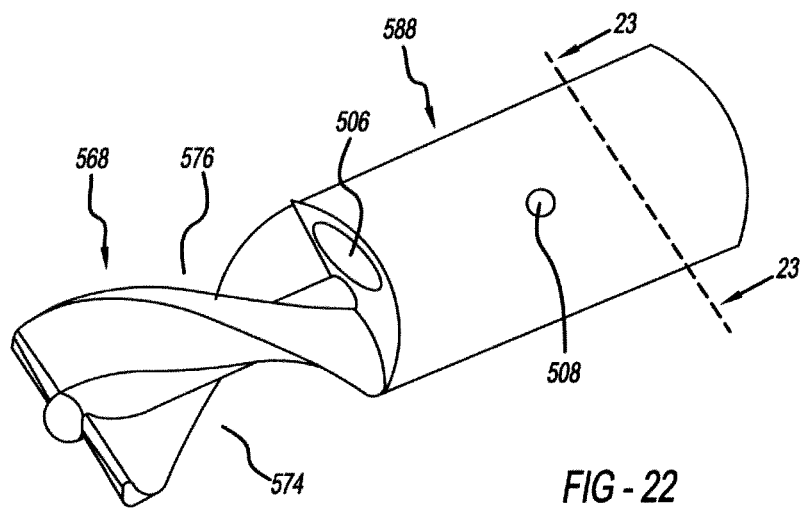
FIG. 22 is a diagrammatic perspective view of a rotor according to a further embodiment of the invention.
Figure 23:
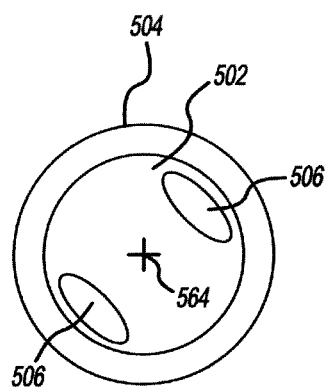
FIG. 23 is a diagrammatic sectional view taking along line 23-23 in FIG. 22.

Merely by way of example, a rotor according to a further embodiment of the invention (FIGS. 22 and 23) includes a helix section 568 as discussed above, but includes a support section 588 in the form of a hollow tubular shell having a single interior bore 502, best seen in FIG. 23, which depicts a cross section view looking from the downstream end of the rotor. The shell also defines a support surface in the form of a cylinder with a full 360° extent around the axis 564 of the rotor. The channels 574 and 576 of the helix section communicate with passage 502 of the support section through ports 506 at the juncture between the support section and the helix section. The particular configuration of the ports 506 in FIGS. 22 and 23 is schematic. Desirably, the ports would have surfaces merging smoothly with the channels defining the helix section. The cylindrical support surface can act as a hydrodynamic bearing surface. To assure continuous washing of the support surface 504 and the interior bore of the housing, holes 508 may be provided through the wall of the tubular support section.

Figure 24:
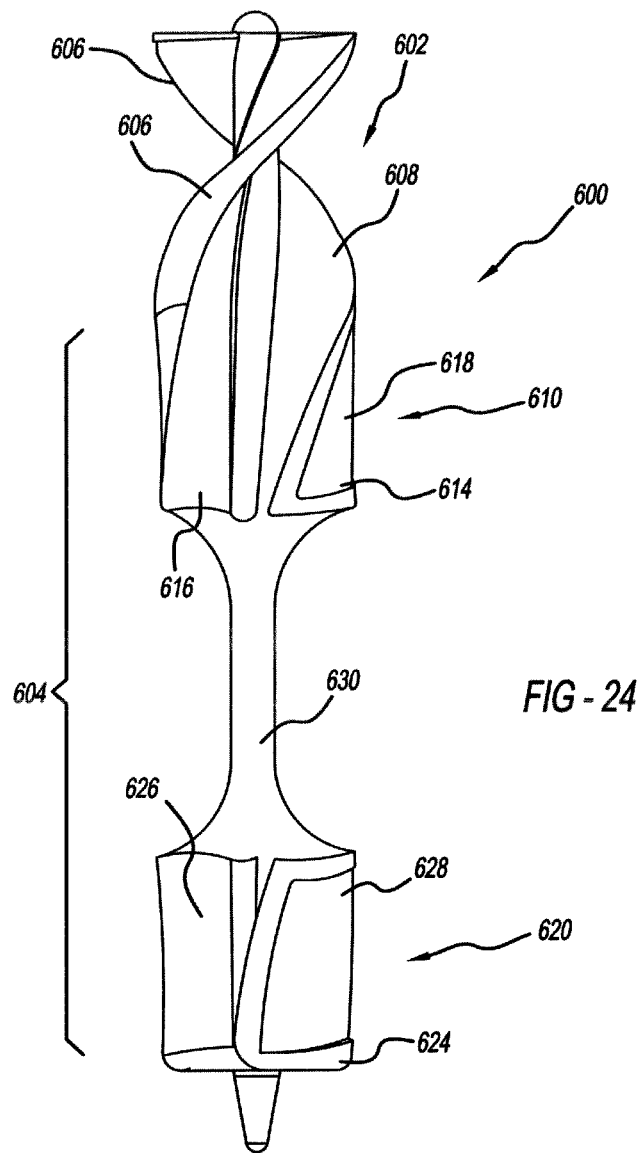
FIG. 24 is a diagrammatic elevational view depicting a rotor according to yet another embodiment of the invention.

Referring to FIG. 24, a rotor 600 according to a further embodiment of the invention includes a helix region 602 with peripheral surface areas 606 and channels 608 similar to those discussed above. The rotor also includes a support region 604. In this embodiment, the support region includes an upstream portion 610, a downstream portion 620 spaced-apart from the upstream portion in the axial direction and a shaft 630 extending between these portions. Upstream portion 610 has lobes 614 and channels 616 between the lobes. Here again, lobes 614 have radially outwardly facing support surfaces which incorporate hydrodynamic bearing surfaces 618. The downstream portion 620 has lobes 624 and passages 626 between the lobes. Lobes 624 define further hydrodynamic bearing surfaces 628. Shaft 630 has a relatively small cross-sectional area. Passages 616 and 626 communicate with the space surrounding the shaft. The small cross-sectional area of the shaft provides a relatively low resistance to axial fluid flow. The axial spacing of the upstream and downstream portions from one another provides a greater axial distance between the hydrodynamic bearing surfaces, and thus provides greater resistance to yaw or tilting of the rotor in directions transverse to the central axis of the housing.

In the embodiments discussed above, each rotor is formed entirely as a unitary body of a single ferromagnetic material. However, this is not essential. For example, the rotor could be formed from a ferromagnetic material such as iron or an iron-nickel alloy, which has desirable ferromagnetic properties, but which is far less compatible with the blood. The rotor may be plated with a metal having desirable blood compatibility of properties such as platinum, with or without one or more intermediate plating layers. In yet another variant, the helix section of each rotor may be formed from a non-ferromagnetic material which is bonded to a support section incorporating a ferromagnetic material.

As these and other variations and combinations of the features discussed above can be utilized, the foregoing description of the preferred embodiments should be taken by way of Illustration rather than by way of limitation of the invention as defined by the claims.

What is claimed is:

1. An implantable blood pump comprising:
   (a) a housing defining a bore having an inlet, an outlet and an axis extending between the ends;
   (b) one or more rotors disposed within the bore coaxial with the bore, each rotor including a permanent magnet;
   (c) one or more stators disposed outside of the bore each opposite a rotor for providing a rotating magnetic field within the bore;
   (d) a first gripper mechanically connected to the housing and to the one or more stators, the first gripper being adapted to engage a wall of an artery and hold the housing and stators in an operative position at least partially within the artery;
   (e) a driveline extending downstream from the pump; and
   (f) a plurality of second grippers along the length of the driveline for maintaining the driveline away from the wall of the artery;
   (g) a plurality of gripper supports attached along the length of the driveline at a predetermined distance from one another, each of the plurality of second grippers associated with one of the plurality of gripper supports,
   the one or more rotors being constructed and arranged so that during operation of the pump the one or more rotors are suspended within the bore of the housing and out of contact with the housing solely by forces selected from the group consisting of magnetic and hydrodynamic forces on the rotors.

2. A pump as claimed in claim 1 wherein the one or more rotors are the only elements of the pump which move during operation.

3. A pump as claimed in claim 1,
   wherein the housing is elongated and has an inlet and an outlet end, and
   wherein at least one of the first and second grippers includes an expansible element connected to the housing adjacent the outlet end.

4. A pump as claimed in claim 3 wherein the expansible element includes a tubular stent.

5. A pump as claimed in claim 3 wherein the housing has an axis and the expansible element includes a plurality of fingers spaced circumferentially around the axis.

6. A pump as claimed in claim 3 wherein the housing has an axis and the expansible element includes first and second spiral springs having an inner end secured to the housing and extending in opposite circumferential directions around the axis of housing.

7. An implantable blood comprising:
   (a) a housing defining a bore having an inlet, an outlet and an axis extending between the ends;
   (b) one or more rotors disposed within the bore coaxial with the bore, each rotor including a permanent magnet;
   (c) one or more stators disposed outside of the bore each opposite a rotor for providing a rotating magnetic field within the bore;
   (d) a first gripper mechanically connected to the housing and to the one or more stators, the first gripper being adapted to engage a wall of an artery and hold the housing and stators in an operative position at least partially within the artery;
   (e) a driveline extending downstream from the pump; and
   (f) a plurality of second grippers attached along the length of the driveline at a predetermined distance form one another for maintaining the driveline away from the wall of the artery,
   the one or more rotors being constructed and arranged so that during operation of the pump the one or more rotors are suspended within the bore of the housing and out of contact with the housing solely by forces selected from the group consisting of magnetic and hydrodynamic forces on the rotors.

\* \* \* \* \*